United States Patent [19]

Taguchi et al.

[11] 4,101,275
[45] Jul. 18, 1978

[54] AUTOMATIC PHOTOMETRIC ANALYZER

[75] Inventors: Isamu Taguchi, Tokyo; Akihiro Ono, Ichigao; Ryutaro Matsumoto, Tokyo, all of Japan

[73] Assignees: Nippon Steel Corporation; Kokoshi Electric Co., both of Tokyo, Japan

[21] Appl. No.: 707,993

[22] Filed: Jul. 23, 1976

Related U.S. Application Data

[60] Division of Ser. No. 575,078, May 6, 1975, Pat. No. 4,003,708, which is a continuation of Ser. No. 511,205, Oct. 2, 1974, abandoned, which is a continuation of Ser. No. 283,851, Aug. 25, 1972, abandoned.

[30] Foreign Application Priority Data

Aug. 26, 1971 [JP] Japan .................................. 46-65729

[51] Int. Cl.² .......................................... G01N 21/26
[52] U.S. Cl. ................................ 23/230 R; 23/253 R
[58] Field of Search .................. 23/230 R, 253 R, 259

[56] References Cited

U.S. PATENT DOCUMENTS

| | | | |
|---|---|---|---|
| 2,879,141 | 3/1959 | Skeggs | 23/253 R |
| 3,690,833 | 9/1972 | Ferrari | 23/253 R |
| 3,694,160 | 9/1972 | Sagusa et al. | 23/230 R |
| 3,700,562 | 8/1972 | Morgenstern et al. | 23/253 R X |
| 3,723,062 | 3/1973 | Dahms | 23/253 R X |

Primary Examiner—R.E. Serwin
Attorney, Agent, or Firm—Toren, McGeady and Stanger

[57] ABSTRACT

In an automatic photometric analyzer, an injector and a coloring source deliver a respective sample solution and a coloring solution to a reactor to form a reactant. The reactant is circulated through an absorbency-measuring photometric device and back to the reactor.

8 Claims, 11 Drawing Figures wave length: 700 mµ
flow cell: 20 mm
reference
 liquid: water wave length: 700 mµ
flow cell: 20 mm
reference
 liquid: water

AUTOMATIC PHOTOMETRIC ANALYZER

This is a division of applicant Ser. No. 575,078, filed May 6, 1975 now U.S. Pat. No. 4,003,708, which in turn is a continuation of application Ser. No. 511,205 filed Oct. 2, 1974, now abandoned, which in turn is a continuation of application Ser. No. 283,851, filed Aug. 25, 1972, now abandoned.

BACKGROUND OF THE INVENTION

This invention relates to photometric analysis.

In principle, photometric analysis is a method of determining the quantity of elements in a sample solution in which the solution color is affected by the elements and specific wave lengths are measured.

Since photometric analysis has great advantages over other set chemical analyses with respect to sensitivity, selectivity, rapidity, etc. much research for analysis methods has been attempted for various kinds of samples.

However, conducting these analyses is complicated and troublesome, requiring much time and expert techniques.

The photometric analysis method may be roughly classified into following five unit steps or operations. These operations are:

(1) Preliminary treating of sample solution,
(2) Adding coloring solutions,
(3) Coloration,
(4) Measuring for absorbency and
(5) Measuring for a blank value.

In some cases, one or two of the above operations may be omitted, but, in principle, the operations are carried out in the above-mentioned order. Quantitative analysis of the elements is calculated from prepared calibration curves.

In case of a solid sample, a dissolving operation is added prior to the operation (1), so that when the solution sample, which is a solution of the solid sample, is used as a starting substance, the operations are the same.

There are two typical types of automatic photometric analyzers on the market. One operates as follows: a sample solution and coloring solution are continuously fed by means of a pump, coloring reactions occur in a feed pipe, and at the end portion of feed pipe apparatus is located for continuously measuring the absorbency. The other type operates as follows: A number of test tubes are successively moved, and a sample solution and coloring solution are successively injected into the test tubes by means of an injection type pump to carry out color reactions. The test tubes then are used as cells for measuring the absorbency, and the absorbency of solutions in the test tubes may be continuously measured.

However, with regard to simplicity, low cost, precision and accuracy of analysis, these type of apparatus are not sufficient for practical use.

SUMMARY OF THE INVENTION

The invention relates to an automatic method and apparatus of photometric analysis, in which usual complicated and troublesome manual operations are simplified.

The object of this invention is to provide a simple, cheap and practical method and apparatus for simplifying photometric analysis.

According to the invention, this object may be attained by a system which is quite different from those on the market. This system employs novel elements of photometric analysis for better results as to precision and accuracy, compared with that obtained by prior manually operated analysis devices.

DESCRIPTION OF PREFERRED EMBODIMENTS

Figure 1:
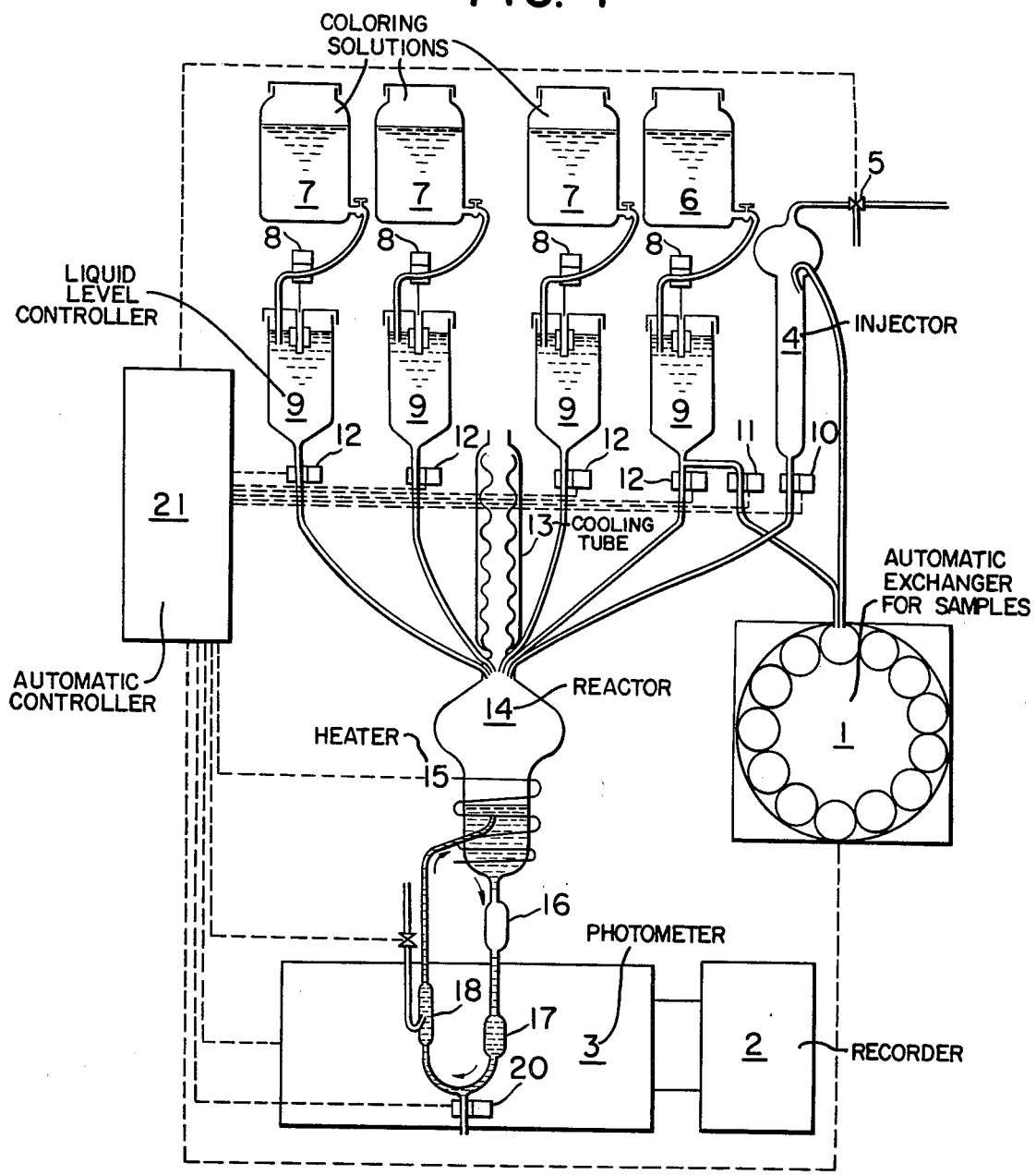
FIG. 1 is an explanatory drawing of apparatus according to the present invention.

In FIG. 1, an automatic exchange 1 automatically exchanges a number of vessels containing the sample solution. In FIG. 1, a turn table system is diagramatically shown, however, other automatic exchange systems, such as a belt conveyor, may be also used. In the exchanger, there is provided a tube connected with an injector for the sample solution and a tube connected with an electromagnetic cock 11, each of the tubes being respectively fixed to elevators of the exchanger. The length of the tip of the tube from its fixed position is determined such that the tip may reach the bottom of the vessel on the exchanger, and a certain portion of the sample solution initially contained in the vessel is fed to the injector 4 by the injector for the sample solution. For this feeding, a vacuum suction or pressure feed or the like may be used.

After the sample solution is supplied, an amount of pure water is poured into the vessel from the tube connected with the electromagnetic cock 11 to rinse the vessel, and the solution is fed to the injector again.

Numeral 2 denotes a recorder.

Numeral 3 indicates a photometer, for which any type may be used. In the light passage area of the photometer, there is arranged a flow cell 17. An air blow pipe 18 circulates the solution, but circulation by means of any small size pump may be used.

An injector designated 4, for the sample solution is made of glass. The sample solution fed from the exchanger 1 and the pure water which rinsed the vessel is temporarily accumulated in injector 4 and an electromagnetic cock 10 is used to inject a solution from injector 4 into a main reactor body 14.

A three way electromagnetic valve 5 between a vacuum pump and the injector changes the flow passages and causes the pressure of the injector for the sample solution to be under vacuum or atmospheric pressure.

Numeral 6 designates a bottle for pure water and numeral 7 bottles for coloring solutions. Bottles of about 500 ml to 3 liters are the most suitable.

In the drawing, numerals 8, 10, 11 and 12, denote electromagnetic cocks, which are opened and closed under control of an automatic controller 21. The electromagnetic cock is used to supply solution from the bottles 6 and 7 to liquid level controllers 9, and the electromagnetic cock 10 is used to supply a sample solution contained in the sample injector 4 and pure water to the reactor 14. The electromagnetic cock 11 is used to supply pure water for rinsing the sample solution remaining in the sample vessel. The electromagnetic cock 12 is used to supply pure water or coloring solution from the liquid level controller 9 to the reactor 14. Numeral 20 denotes an electromagnetic cock for discharging the waste solution.

The reproducibility of an addition mechanism by using bottles 6, 7, electromagnetic cocks 8, liquid level controllers 9 and electromagnetic cocks 12 according to the present invention was investigated, the results of which are shown in Table 1 below.

Four sets of the addition mechanisms are prepared by filling all bottles (made of polyethylene, capacity 1 liter) with water. As shown in FIG. 1, the electromagnetic cock on the lower portion of the liquid level controller was opened for 30 seconds, and water was received by measuring cylinder through narrow tubes on the lower portion of cooling pipe and was measured.

According to Table 1, the amount of water to be added within 30 seconds is somewhat different for each addition mechanism, however, the reproducibility of addition mechanism is good compared with the case in which the addition is carried out manually by using a pipet. A cooling tube 13 in FIG. 1 forms a portion of the reactor 14 where the sample solution is prevented from being lost by heat.

Table 1

| Addition mechanism | The reproducibility of added solution due to an addition mechanism (ml, water used) | | | | | |
|---|---|---|---|---|---|---|
| | 1st | 2nd | 3rd | 4th | 5th | Mean |
| No. 1 | 32.1 | 32.0 | 32.0 | 32.0 | 32.2 | 32.1 |
| No. 2 | 33.0 | 28.1 | 28.0 | 28.2 | 28.1 | 28.1 |
| No. 3 | 33.0 | 33.1 | 32.9 | 33.0 | 33.0 | 33.0 |
| No. 4 | 29.5 | 29.5 | 29.5 | 29.7 | 29.6 | 29.6 |

The portion where the coloring reaction and measurement according to the present invention are carried out (hereinafter called coloring reaction and measuring portion), contains a temperature control device so that heating by heater 15 or cooling by water may be effected according to the conditions for coloring.

As will be seen from FIG. 1, the coloring reaction and measuring portion is composed of a circulation tube starting from the lower portion of the reactor and returning to its central portion, and quantities of sample solution and coloring solution are added for set time periods into the reactor 14. The coloring reaction and coloring solution is circulated by air from the blow pipe and during circulation, bubbles in the circulating solution are removed by means of a bubble-eliminating tube 16, and absorbency of the solution as to the coloring reaction is measured continuously by a flow cell 17 and photometer 3.

The function of the coloring reaction portion will be explained in detail hereinafter.

The sample solution injected into the reactor 14 reacts with coloring solutions added afterwards to produce a color, however, this reaction sometimes requires considerable time at room temperature and in some cases, it is necessary to keep the temperature constant. Therefore, to accelerate the reaction, a heating device is applied to the outer wall or temperature control such as by cooling or by a simple thermostat is achieved. For carrying out a uniform reaction, it is desirable to circulate the solution and stir it. The circulation of the solution by means of this circulation tube not only assures the stirring action of the solution, but also meets the first object that the means absorbency of the solution is continuously measured by the flow cell 17. Thus, by using the circulation tube, both the heating effect of the heating on the photometer and the effect of air bubbles generated or mixed in the solution may be removed at the same time. This solution is circulated in the direction of the arrow in FIG. 1. Circulation is achieved by an air blow pipe (instead of air, other gases such as an inert gas may be used) having a simple construction.

In this air blow pipe, an air blow nozzle is directed inwardly and the device is very small in size, simple in construction and low in cost, but nevertheless, rapid circulation of solution may be assured. The air blown in by means of this blow pipe prevents sudden boiling of the solution in case it is heated by the heater in the reactor.

It is possible to replace the air blow pipe construction described above by a pump, however, no such pump of small size, low cost which is also acid-proof is presently available.

An aspect of the invention involves attaching a bubble eliminating tube 16 to this circulatoin pipe. The elimination tube is made merely by enlarging a lower portion of the reaction pipe to a diameter of about twice the prior size. Bubbles mixed in the solution by the circulation mixing and bubbles generated by heating are completely removed within the elimination tube and never reach the flow cells, so that the measurement of absorbency will not be disturbed.

Numeral 21 in FIG. 1 denotes an automatic controller.

Although a detailed explanation is given above for the photometric analyzer according to the present invention, further features of the analyzer are that a number of sample solutions are mounted on the automatic exchanger 1 in FIG. 1, while all of other analysis operations are automatically carried out by means of the automatic controller 21 to record the results of the analysis.

In the analyzer according to the present invention, the change of the absorbency with respect to time is recorded, the results of which may be digitally typed out by using a computer. As shown by the dotted lines in FIG. 1, the automatic controller 21 is connected with the sample solution automatic exchanger 1, photometer 3, three-way electromagnetic valve 5, electromagnetic cocks 10, 11, 12, heater 15, electromagnetic valve 19 and electromagnetic cocks 20 and automatically controls the exchange of sample solution, suction to the injector for sample solution, addition of sample solution to the reactor, injection of pure rinsing water into the vessel filled with the sample solution, addition of pure water and coloring solution to the reactor, heating, blow-in of the air to the circulation pipe, and the discharge of water, etc.

In this analyzer, a program timer of a rotary drum system is used as the automatic controller, however, all of conventional program timers, for example, pin-board system and Seakens programmer may be also used. The programs will be mentioned in detail in the followng examples, however, they are determined experimentally for every constituent and sample to be analyzed.

EXAMPLE 1

Phosphorus Analysis

Figure 2:
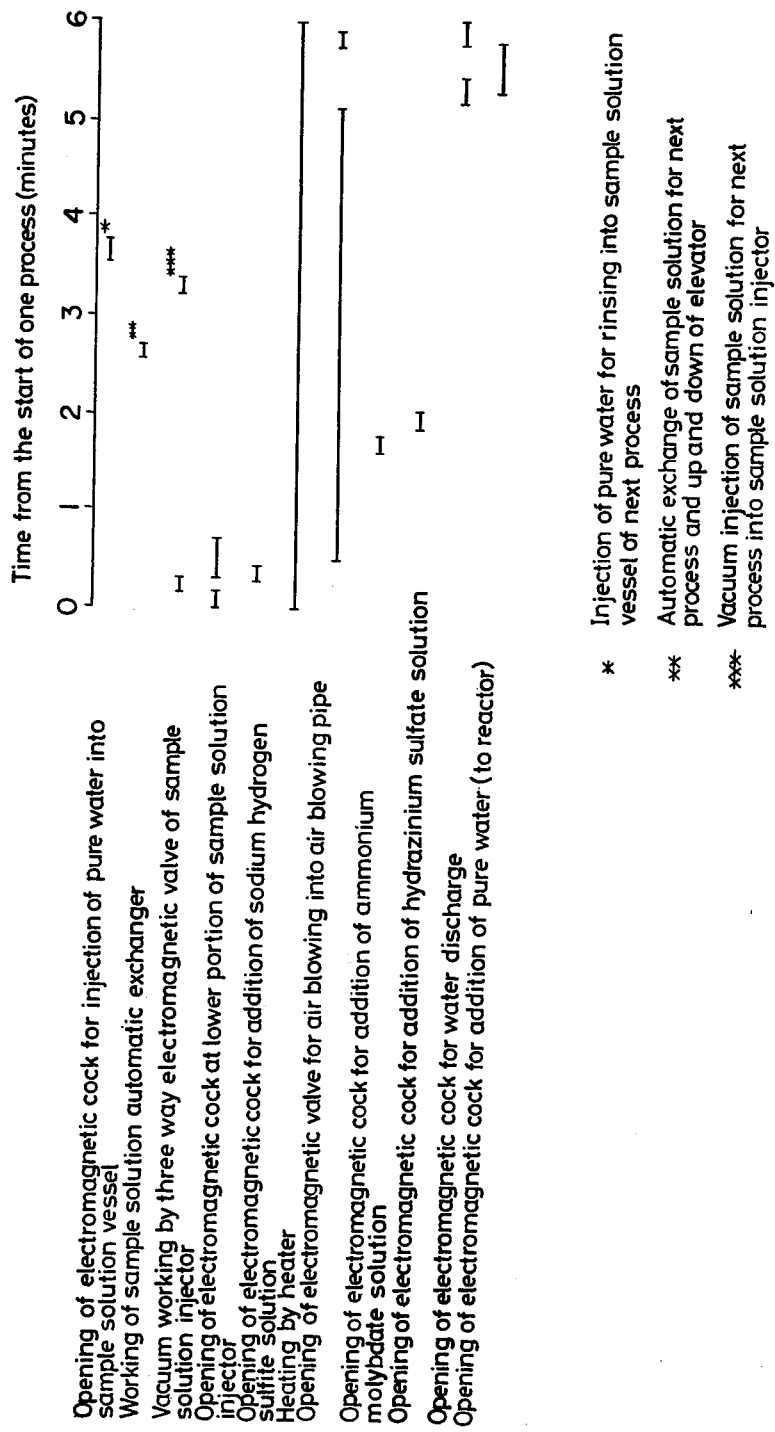
FIG. 2 is a method for analysis of phosphorus by means of the apparatus according to the present invention.

There are a number of photometric analytical methods for phosphorous, however, most of them are carried out by hydrazin sulfate reduction molybdenum blue. To carry out phosphorus analysis by this method, three bottles are used for the coloring solution. Three kinds of solutions are placed in the bottles respectively. These are sodium hydrogen sulfite solution (20%), ammonium molybdate solution (25 g of ammonium molybdate is dissolved in 375 ml of sulfuric acid and water, and diluted with 1 liter of water, and hydrazin sulfate solution (0.15%). All of other apparatus are those explained above in FIG. 1. As shown in FIG. 2, an analysis program or method is made as one process for a total of 6 minutes.

FIG. 2 shows how the respective automatic control is practiced. This program is made by determining the optimum analysis conditions from the results of fundamental experiments or phosphorus analysis according to the present invention.

Figure 3:
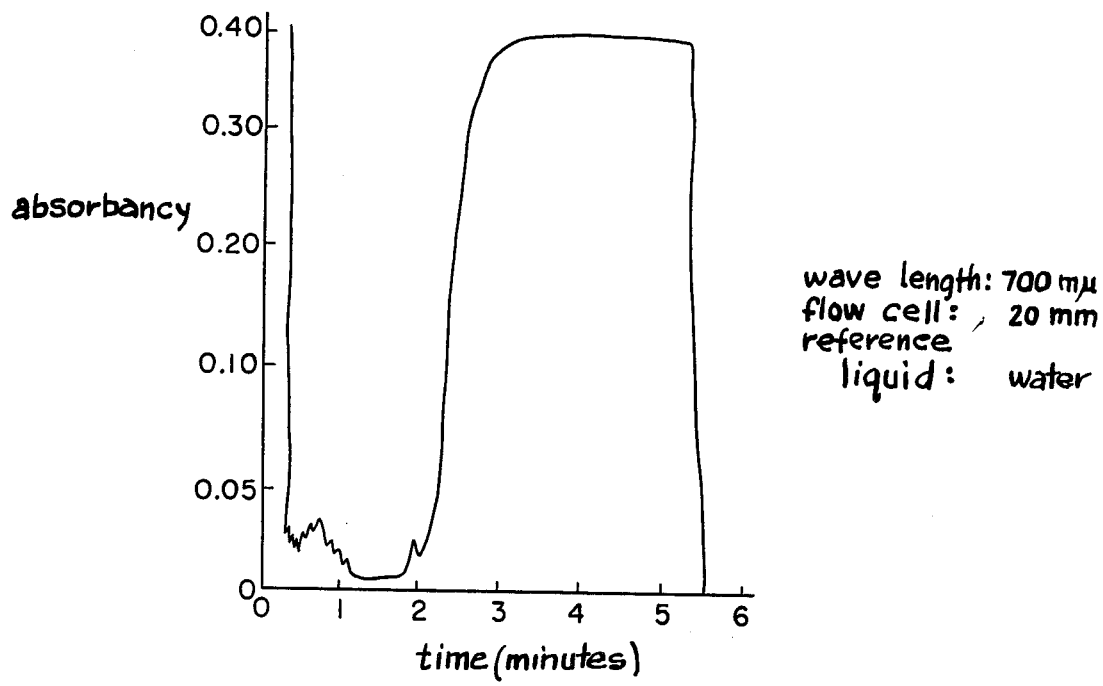
FIG. 3 is a diagram showing the relationship between absorbency and time found in the apparatus according to the present invention.

In FIG. 3, a chart is presented of the time change of absorbency within six minutes of one process which is recorded, by using phosphorus solution, according to the program of FIG. 2. The apparatus according to the present invention is used to practice the method of FIG. 2 and FIG. 3 is explained hereinafter.

As mentioned above, the sample solution and pure water after rinsing are injected into the reactor and the solution enters into the lower portion of the reactor and the circulation pipe. During this injection step, sodium and reactant are electrically heated.

After the addition step of sodium hydrogen sulfite solution is finished, the air blowing into the pipe is started and the circulation of the solution begins.

With a time lapse, the absorbency becomes nearly stable. This stable absorbency is attributable to the added sodium hydrogen sulfite solution, and if any colored ion such as nickel ion and chromium ion, etc. is contained in large quantity, the absorbency will become stronger. Since this absorbency is not attributed to the phosphorus which is being measured, it must be deducted from the measured value and is the so-called blank value. The blank value to be deducted from this measured value should be corrected from the quantity of solution at the time of measurement and of the finally measured value. In succession, as seen from FIG. 2, ammonium molybdate solution and hydrazin sulfate solution are added. After a time, the formation of molybdenum blue occurs, the absorbency increases and becomes constant after about three minutes from the beginning. Conservatively absorbency is measured at about five minutes. Thereafter, the discharge of the liquid and the rinsing operations of the reactor and of the inside wall of the circulation pipe occurs.

Figure 4:
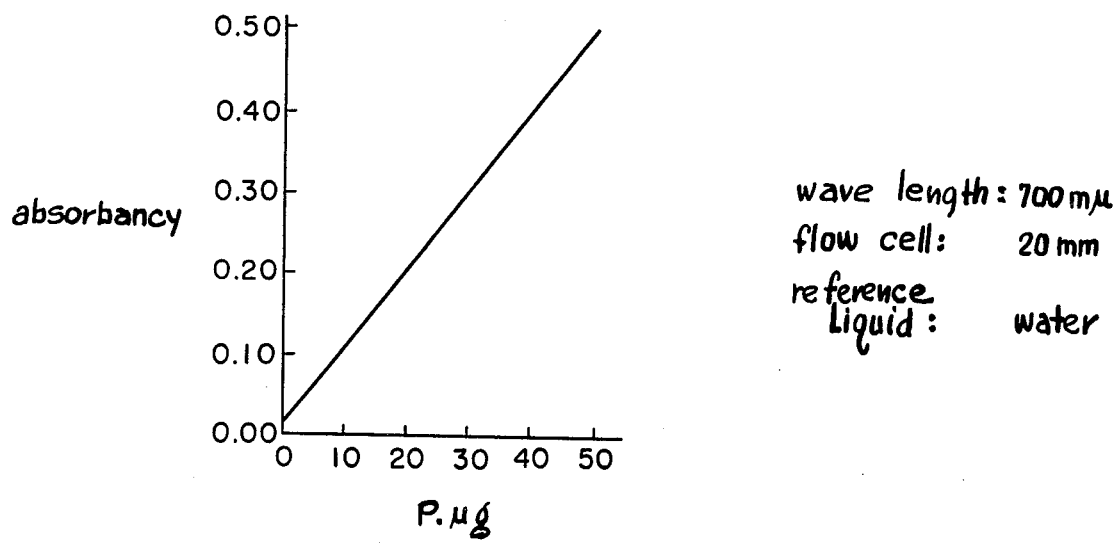
FIG. 4 is a diagram showing an example of a calibration curve for phosphorus by means of the same apparatus.

According to the present apparatus and the program of FIG. 2, various solutions which are added stepwise with standard phosphorus solution are subject to the coloring reaction, measuring the absorbency, making the calibration curve for phosphorus analysis according to the present apparatus, and the result thereof is shown in FIG. 4. It has been proved that the calibration curve of FIG. 4 has good linearity and is sufficiently practical. When 0.1 g of iron exists as an ion in the solution, the calibration curve was not changed. According to the calibration curve, the phosphorus analysis was made for a steel sample (the analysis was carried out after making a sample solution by decomposition with acid), of which the results were compared with the results of phosphorus analysis carried by the manually operated molybdenum blue absorbency method and is shown in Table 2.

Table 2

| Results of phosphorus analysis (%) in steel sample according to the apparatus of the present invention and prior method. | | |
|---|---|---|
| Name of Sample | Results by the Present Apparatus | Results by Manual Operation |
| No. 1 | 0.011 | 0.011 |
| No. 2 | 0.021 | 0.021 |
| No. 3 | 0.037 | 0.037 |
| No. 4 | 0.003 | 0.003 |
| No. 5 | 0.024 | 0.024 |
| No. 6 | 0.115 | 0.114 |
| No. 7 | 0.040 | 0.039 |
| No. 8 | 0.045 | 0.045 |

According to Table 2, it is evident that the analysis by the present apparatus compares well with that of the manual operation.

The phosphorus analysis by prior manual operation takes about 40 minutes for one process, while the phosphorus analysis by the apparatus according to the present invention takes only 6 minutes and because of automatic operation, no special skill is required therefor.

EXAMPLE 2

Manganese Analysis

In the following explanation, those parts overlapping with the explanation in Example 1 are omitted. There are a number of photometric analyses methods available for manganese, however, most of these analyses involve the periodic acid oxidation photometric method. To carry out manganese analysis by this method, two bottles of coloring solution are used and two kinds of solution are placed herein respectively. These are urea (5%) - silver nitrate (2%) solution and sodium periodate solution (5%). The apparatus in FIG. 1 is employed. Analysis program is set forth in FIG. 5 and one process takes 6 minutes.

Figure 5:
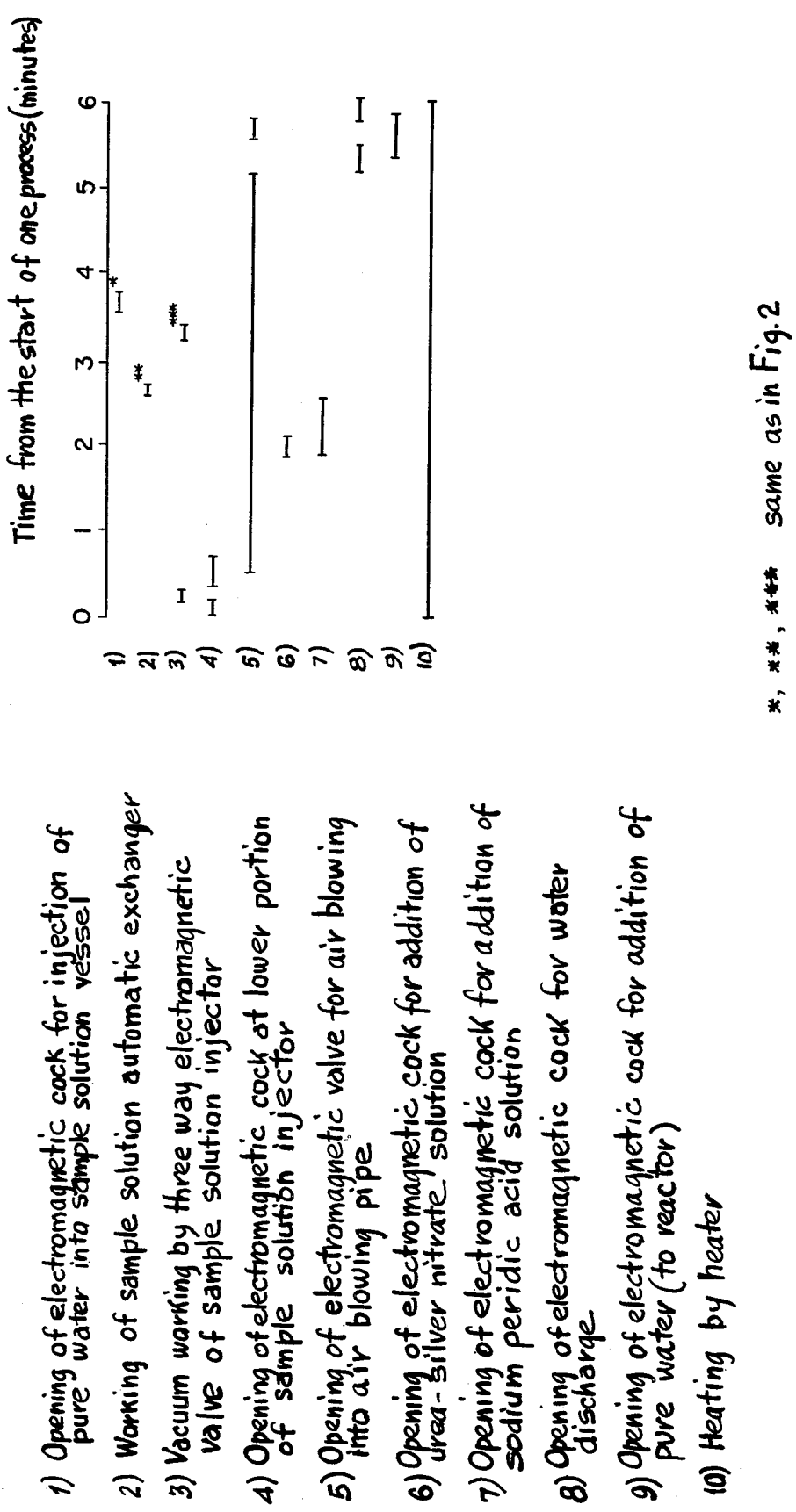
FIG. 5 is a method for analysis of manganese by means of the apparatus according to the present invention.

By means of the present apparatus, according to the program of FIG. 5, and by using manganese solution (quantity of manganese: 500μg) the change of absorbency with time within 6 minutes for one process was recorded. The results were similar to the case of FIG. 3 of Example 1, and the absorbency of the solution became constant after about 2 minutes and 40 seconds after one process was started. However, when chromium ion and the like coexist in the sample solution, coloring will be delayed, so that for safety the measuring value was obtained after 5 minutes elapsed after one process was started. The blank value is corrected prior to the measuring of the value in the range of one to one half minutes after starting, when the absorbency becomes constant, similar to Example 1.

Figure 6:
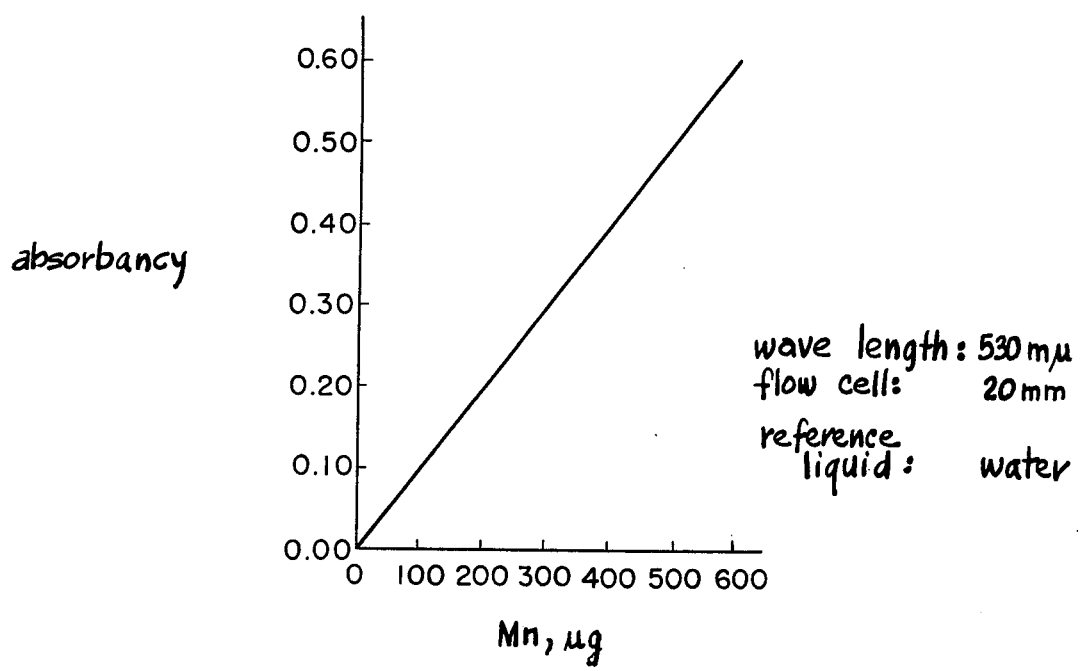
FIG. 6 is a diagram showing an example of a calibration curve for manganese by means of the same apparatus.

A calibration curve made for standard manganese solution, according to the present apparatus and the program of FIG. 5, and is shown in FIG. 6. It has been proved that the calibration curve of FIG. 6 has good linearity and is sufficiently practical. By means of the present apparatus and according to the program in FIG. 7 and the calibration curve of FIG. 6, manganese in a river water sample is analyzed, of which the results are shown in Table 3, which are compared with the results of manual analysis by the periodic acid oxidation photometric method.

Table 3

Results of analysis of manganese in river water (ppm) by means of the apparatus according to the present invention compared with the periodic acid oxidation photometric method.

| Name of sample | Results by means of the present apparatus | Results by manual operation |
| --- | --- | --- |
| No. 1 | 0.10 | 0.10 |
| No. 2 | 0.23 | 0.22 |
| No. 3 | 0.05 | 0.06 |
| No. 4 | 0.07 | 0.07 |
| No. 5 | 0.18 | 0.18 |
| No. 6 | 0.21 | 0.21 |

According to the results of Table 3, it is seen that the results of analysis by means of the present apparatus closely coincides with that of manual operation.

The manganese analysis by the manual operation process takes about 30 minutes for one process, while the manganese analysis by the apparatus according to the present invention takes only 6 minutes and because of the automatic operation, no special skill is required therefor.

EXAMPLE 3

Aluminum Analysis

Analysis, by means of the apparatus, for microaluminum in a sample solution follows. However, those parts overlapping the explanation in Examples 1 and 2 above are omitted. There are a number of photometric analyses for micro-aluminum, however, most of them involve the eriochromecyanin R photometric method. To determine aluminum by this method, three bottles of coloring solution are used and three kinds of solution placed therein respectively. These are thioglycollic acid solution (3%), eriochromecyanin R solution (0.05%) and polycyclic keto-amin solution (320 g of ammonium acetate and 20 g of sodium sulfite are dissolved in 1 liter of water and 3 ml of polycyclic keto-amin is added and stirred up). Others are same as those explained in FIG. 1. The analysis program is determined as in FIG. 7 and one process is set to take 6 minutes.

Two items should be mentioned specially, as compared with Examples 1 and 2. One is that in Examples 1 and 2, the circulation of the solution was carried out by blowing the air into the pipe, while in this example for aluminum analysis, the air is replaced by nitrogen. As mentioned above, the program of FIG. 7 is made from the results of fundamental examination of aluminum analysis by means of the present apparatus. However, it was seen that when iron ion coexisted in the sample solution, the ion was oxidized by the air and iron trivalent ion is produced, resulting in an analytical error, so that the air was replaced by nitrogen, which is inert gas. In this manner, it is very easy for apparatus shown in FIG. 1 to make the reactor and the inside of circulation pipe contain an atmosphere of inert gas, which may be considered as one feature of the present apparatus which compared with the manually operating analysis in which it is very difficult to carry out the color reaction in an atmosphere of inert gas.

The other special matter is that in the eriochromecyanin R photometric method, it takes a long time for perfect coloring, and therefore, constant absorbency is not easily obtained causing analytical error to occur by manual analysis. By means of the present apparatus, the absorbency after a constant time from the start of analysis of one process may be measured, so that a correct analysis may be carried out without any analytical error. The above matters will be explained in further detail from FIG. 8, wherein the time change of absorbency of aluminum according to the program of FIG. 7 by means of the present apparatus as shown.

Figure 8:
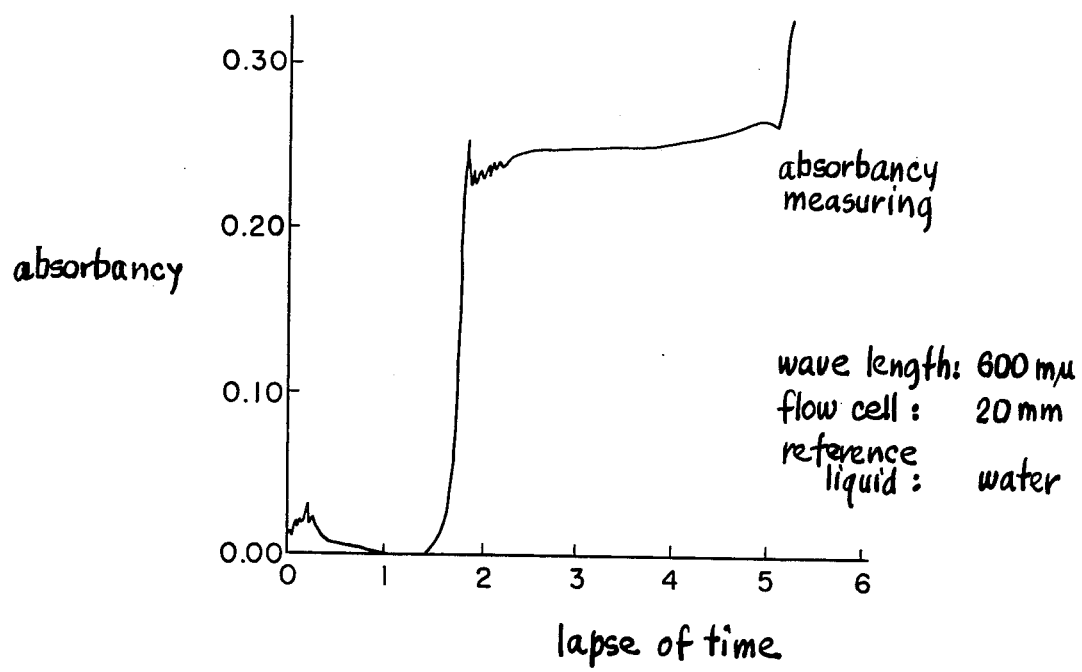
FIG. 8 is a record chart of time change of absorbency (in case of aluminum analysis) by means of the apparatus according to the present invention.

The reaction among aluminum, eriochromecyanin R solution and polycyclic keto-amin solution is slow, and even after 5 minutes from the start of analysis of one process, the absorbency is raised higher, as seen from FIG. 8. Therefore, it has been prepared so that the solution is discharged after 5 minutes and 5 seconds from the start of analysis of one process, thus the absorbency of the solution is read just before that time. When the reproducibility of the measured value of the absorbency is examined, it is seen that the property of reproducibility is very good and sufficiently practical. The usual analysis carried out by manual operation is based on the premise of perfect coloring of the sample solution and coloring solution and methods have been developed therefor. Nevertheless, for some analytical constituents, no coloring solution and methods have been found to the present. Therefore, by means of the present apparatus, the constituent may be analyzed even though it is not always perfectly reacted with coloring solution, this point deserving special mention.

Figure 7:
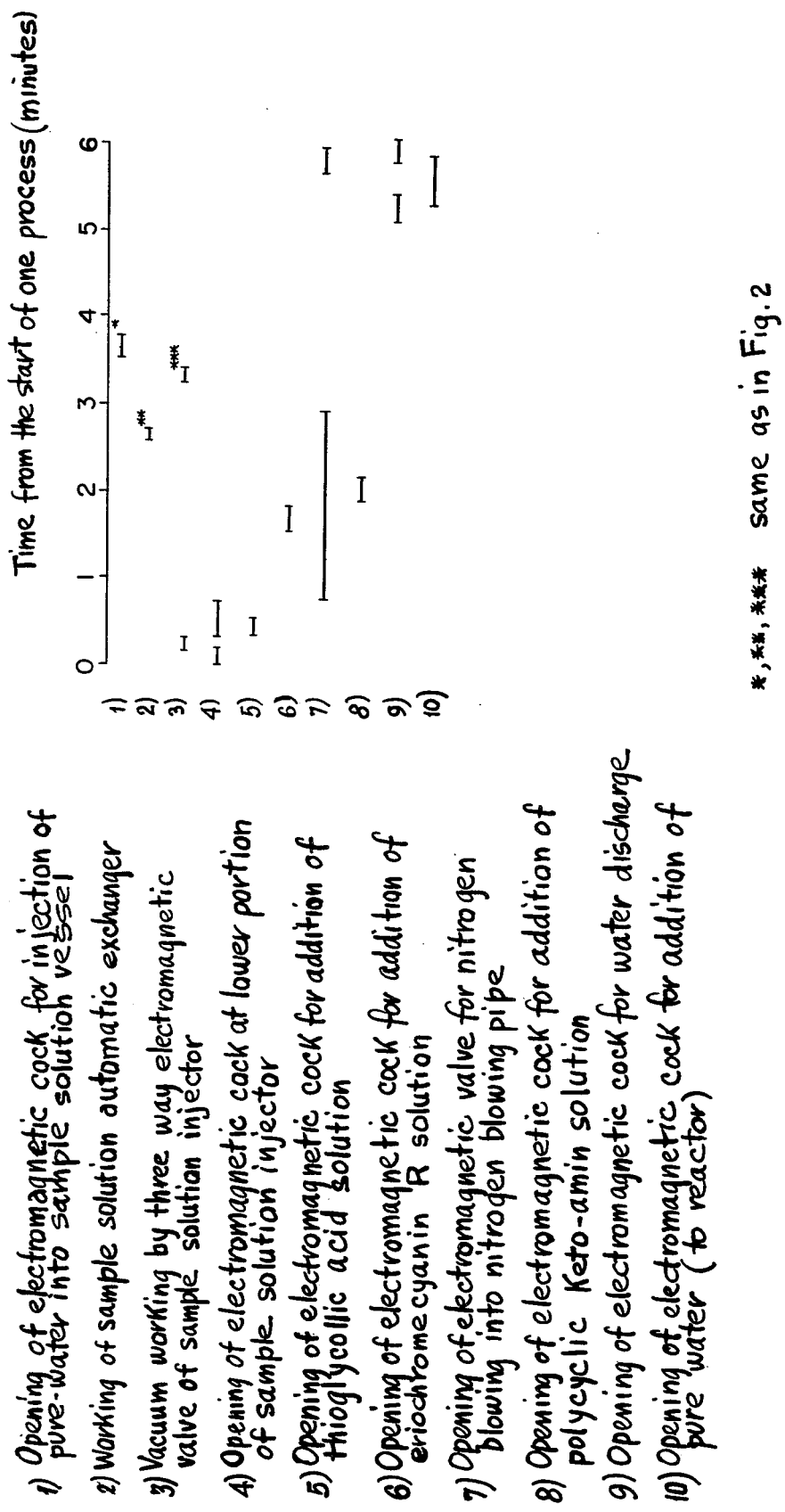
FIG. 7 is a method for analysis of aluminum by means of the apparatus according to the present invention.
Figure 9:
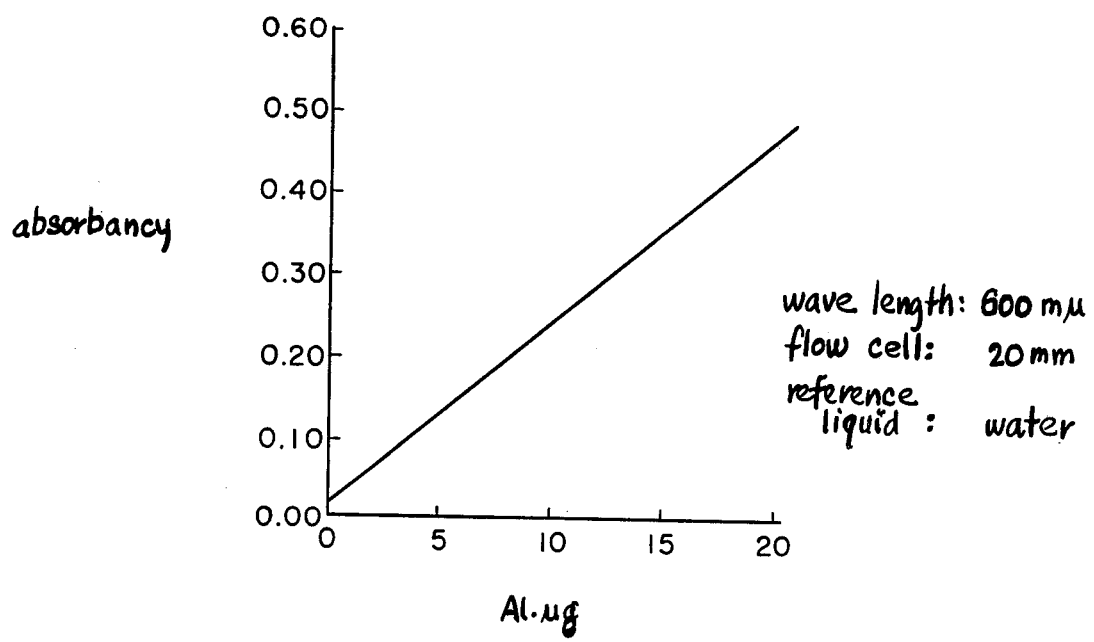
FIG. 9 is a diagram showing an example of a calibration curve for aluminum by means of the same apparatus.
Figure 10:
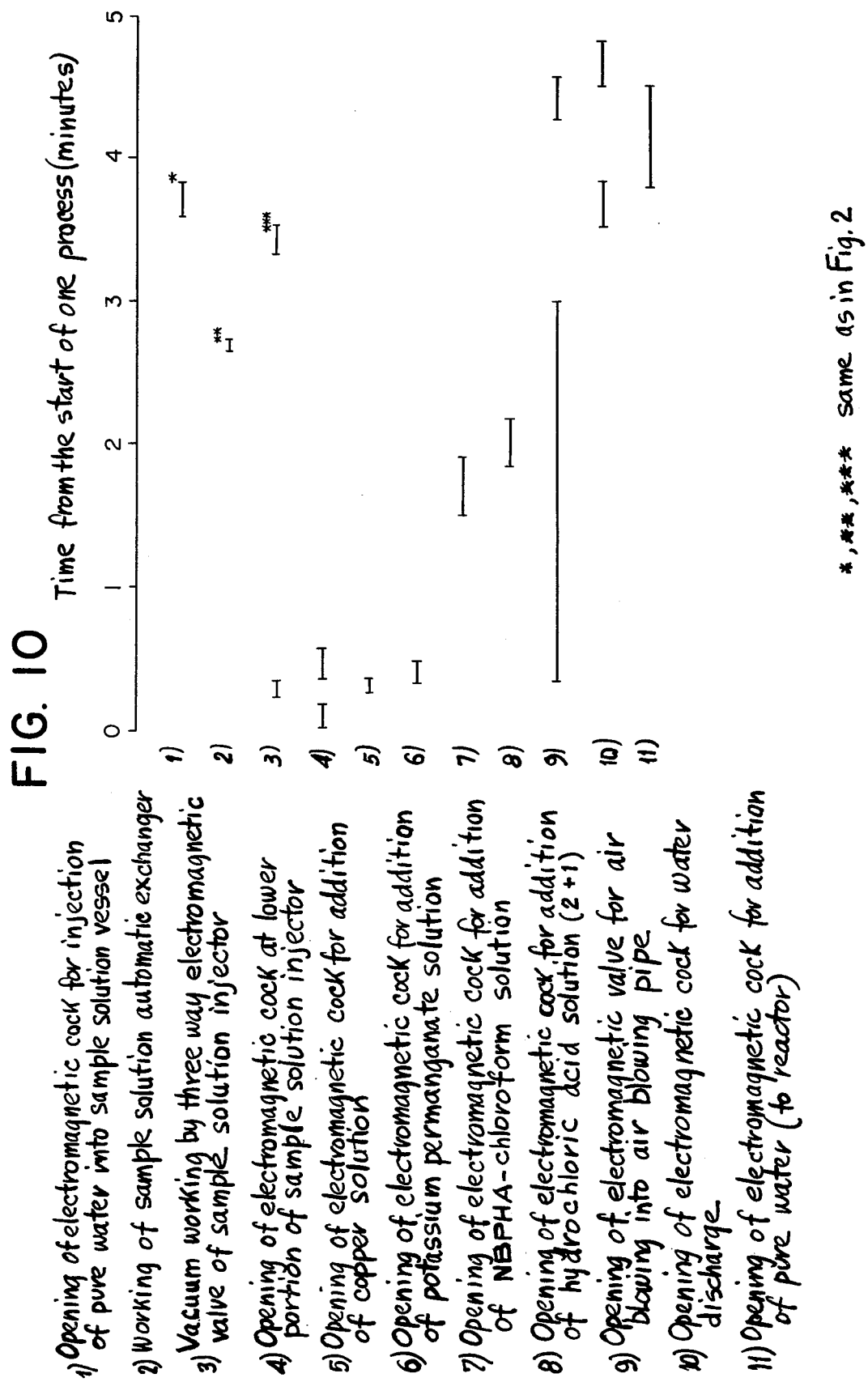
FIG. 10 is a graph illustrating steps performed according to an aspect of the invention.
Figure 11:
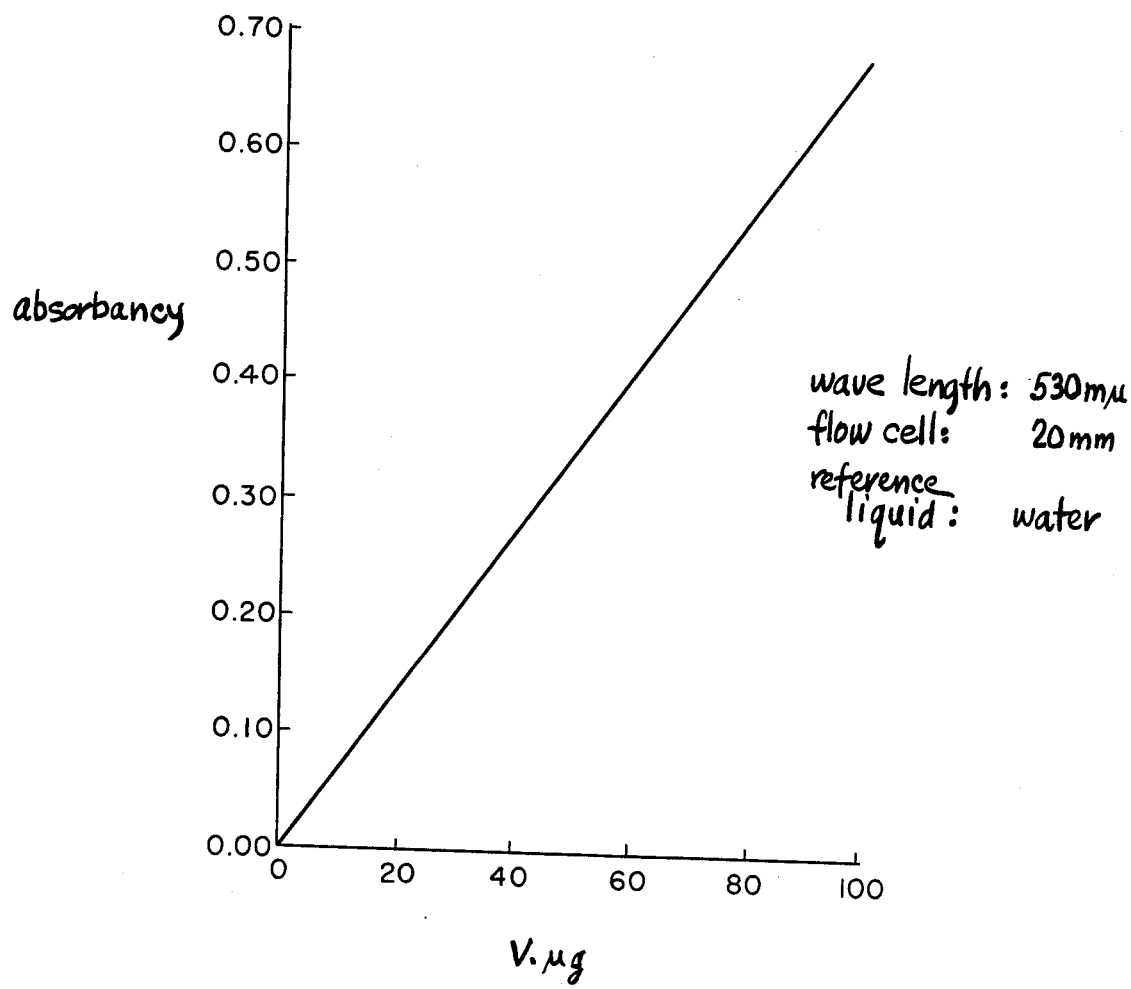
FIG. 11 is a graph comparing absorbency with weight of vanadium.

According to the present apparatus and the program of FIG. 7, various water solutions added stepwise with standard aluminum solution are colorized, and the absorbency is measured. A calibration curve for aluminum analysis by means of the present apparatus is made as shown in FIG. 9. It has been proved that the calibration curve of FIG. 9 has good linearity and is sufficiently practical. By means of the present apparatus and according to the program of FIG. 7 and the calibration curve of FIG. 9, aluminum in a city water sample is analyzed, the results of which are shown in Table 4 in comparison with that of an analysis by the manually operated eriochromecyanin R photometric method.

Table 4

Results of comparison of analysis of aluminum in city water (ppm) by means of apparatus according to the present invention and prior art manually operated eriochromecyanin R photometric method

| Name of sample | Results by means of the present apparatus | results by manual operation |
| --- | --- | --- |
| No. 1 | 0.08 | 0.08 |
| No. 2 | 0.02 | 0.02 |
| No. 3 | 0.01 | 0.01 |
| No. 4 | 0.03 | 0.03 |
| No. 5 | 0.03 | 0.02 |
| No. 6 | 0.09 | 0.09 |
| No. 7 | 0.02 | 0.02 |
| No. 8 | 0.07 | 0.07 |

According to the results of Table 4, it is seen that the results of analysis by means of the present apparatus coincided closely with that of a manual operation and is sufficiently correct and practical.

The aluminum analysis by manual operation takes about 40 minutes for one process, while the aluminum analysis by the apparatus according to the present invention takes only 6 minutes and because of the automatic operation, no special skill is required.

We claim:

1. A photometric batch type analysis method, comprising, feeding a sample solution and a coloring solution to a reactor form a reaction product, then feeding said reaction product to a recirculation system in which the reaction product is expanded to eliminate bubbles, measuring its absorbency and forcing the reaction product back into the reactor by air pressure, removing the reaction product from said recirculation system after its absorbency has been measured a selected number of times.

2. A method as set forth in claim 1, comprising controlling the temperature of the circulating reaction product.

3. A method as set forth in claim 2, comprising heating the circulating reaction product.

4. A method as set forth in claim 1, comprising an automatic exchanger from which sample solutions are supplied, injecting said sample solution from said exchanger to said reactor, said injector step being automatically controlled.

5. A method as set forth in claim 1, wherein bubbles are formed in the reaction product when the reaction product is circulated and comprising the step of eliminating said bubbles from said reaction product.

6. A method as set forth in claim 4, comprising controlling the temerature of the circulating reaction product.

7. A method as set forth in claim 1, comprising heating the circulating reaction product.

8. A method as set forth in claim 1, comprising recording the analysis of the reaction product.

* * * * *

UNITED STATES PATENT OFFICE
CERTIFICATE OF CORRECTION

Patent No. 4,101,275      Dated July 18, 1978

Inventor(s) ISAMU TAGUCHI, et al

It is certified that error appears in the above-identified patent and that said Letters Patent are hereby corrected as shown below:

In the heading of the Patent [73] should read as follows:

[73] Assignees: Nippon Steel Corporation; Kokusai Electric Co., both of Tokyo, Japan Signed and Sealed this Twentieth Day of March 1979

[SEAL]

Attest:

RUTH C. MASON
*Attesting Officer*

DONALD W. BANNER
*Commissioner of Patents and Trademarks*